United States Patent [19]

Henry et al.

[11] Patent Number: 5,736,542
[45] Date of Patent: Apr. 7, 1998

[54] PHARMACEUTICAL COMPOSITIONS CONTAINING A STAUROSPORINE

[75] Inventors: Roy Lindsay Allen Henry; Graham Paul Matthews, both of Horsham, England

[73] Assignee: Novartis Corporation, Summit, N.J.

[21] Appl. No.: 343,404

[22] Filed: Nov. 22, 1994

[30] Foreign Application Priority Data

Dec. 11, 1993 [GB] United Kingdom .................. 9325395

[51] Int. Cl.$^6$ ........................................... A61K 31/55
[52] U.S. Cl. .................................................. 514/211
[58] Field of Search ..................................... 514/211

[56] References Cited

U.S. PATENT DOCUMENTS 5,093,330  3/1992  Caravetti et al. ................... 514/211

FOREIGN PATENT DOCUMENTS 9217181  10/1992  WIPO .

OTHER PUBLICATIONS

Remington's Pharmaceutical Sciences, 15th ed. 1975 Mack Publishing Co., p. 1535.

*Primary Examiner*—Phyllis G. Spivack
*Attorney, Agent, or Firm*—Marla J. Mathias; Karen G. Kaiser

[57] ABSTRACT

An orally administrable pharmaceutical composition comprising a solution or dispersion of a staurosporine active ingredient in a solid saturated polyalkylene glycol glyceride, such as a mixture of esters of $C_8$–$C_{18}$ saturated fatty acids with glycerol and polyethylene glycol, is disclosed that may be administered in capsules or as a dispersion in an aqueous medium.

20 Claims, No Drawings

PHARMACEUTICAL COMPOSITIONS CONTAINING A STAUROSPORINE

This invention relates to pharmaceutical compositions, particularly pharmaceutical compositions comprising a staurosporine as active ingredient.

U.S. Pat. No. 5,093,330 describes staurosporine and N-substituted derivatives thereof as pharmaceuticals for use in tumour inhibition and inflammation inhibition, for antibacterial use and for use in combating arteriosclerosis, diseases of the cardiovascular system and of the central nervous system.

Many staurosporines have low solubility in water. For example, N-benzoylstaurosporine, an especially preferred compound, has a solubility of less than 0.1 mg/liter. The staurosporines have been found to have low or negligible bioavailability.

The formulation of an orally administrable preparation has proved problematic since formulation with materials which are conventionally used to improve bioavailability, including materials in which the staurosporines are soluble, has negligible or no effect on bioavailability.

It has now been found that by dispersing a staurosporine active ingredient in a saturated polyglycolysed glyceride, i.e. a polyalkylene glycol-modified saturated fatty acid glyceride, bioavailability can be considerably increased and orally administrable formulations can be prepared.

Accordingly, the present invention provides a pharmaceutical composition comprising a solution or dispersion of a staurosporine active ingredient in a saturated polyalkylene glycol glyceride.

The staurosporine active ingredient may be any of those described in U.S. Pat. No. 5,093,330. Preferred compounds are N-acylstaurosporines including N-benzoylstaurosporine, N-(3-nitrobenzoyl)staurosporine, N-(3-fluorobenzoyl) staurosporine, N-trifluoroacetylstaurosporine, N-phenylcarbamoylstaurosporine, N-(3-carboxypropionyl) staurosporine, N-methylaminothiocarbonylstaurosporine, N-tert-butoxycarbonylstaurosporine, N-(4-carboxybenzoyl) staurosporine, N-(3,5-dinitrobenzoyl)staurosporine, N-(2-aminoacetyl)staurosporine, N-alanylstaurosporine and their pharmaceutically acceptable salts. An especially preferred active ingredient is N-benzoylstaurosporine.

The saturated polyalkylene glycol glyceride may be, for example, a mixture of glyceryl and polyethylene glycol esters of one or more long chain saturated fatty acids, usually $C_8$–$C_{18}$ saturated fatty acids. The acid component of such esters may be, for example, caprylic acid, capric acid, lauric acid, myristic acid, palmitic acid, stearic acid or a mixture of two or more thereof. The polyethylene glycol component of such esters generally has a molecular weight of 200 to 2000, preferably 1000 to 1800, especially 1400 to 1600. The glycerides, i.e. the glycol-modified glycerides, are usually mixtures of mono, di and triglycerides and polyethylene glycol mono and diesters.

Preferred polyalkylene glycol glycerides are those having a high Hydrophilic-Lipophilic Balance (HLB) value. Further preferred are glycerides which are mixtures of esters of one or more $C_8$–$C_{18}$ saturated fatty acids with glycerol and a polyethylene glycol having a molecular weight of 1000 to 2000, preferably 1200 to 1800, especially 1400 to 1600. An especially preferred material is available commercially from Gattefossé as Gelucire 44/14; this is a mixture of esters of $C_8$–$C_{18}$ saturated fatty acids with glycerol and a polyethylene glycol having a molecular weight of about 1500, the specifications for the composition of the fatty acid component being, by weight, 4–10% caprylic acid, 3–9% capric acid, 40–50% lauric acid, 14–24% myristic acid, 4–14% palmitic acid and 5–15% stearic acid.

The saturated polyalkylene glycol glycerides are either commercially available or may be prepared by known procedures. For example they may be obtained by partial alcoholysis of hydrogenated vegetable oils using the polyalkylene glycol, or by esterification of the saturated fatty acid, or mixture of such acids, using glycerol and the polyalkylene glycol.

In compositions of the invention, the staurosporine active ingredient is generally present in an amount from 1 to 30%, preferably 5 to 25%, especially 10 to 20%, by weight of the composition.

The compositions of the invention may also contain carriers or adjuncts such as those described in U.S. Pat. No. 5,093,330 or other conventional excipients. For oral administration, the composition may be contained in capsules, usually hard capsules of gelatin or soft capsules of gelatin mixed with a plasticiser such as glycerol or sorbitol, or may be used as a dispersion in an aqueous medium, such as water, saline solution or a mixture of water with another, water-miscible, pharmaceutically acceptable solvent, for example in an amount of 0.5 to 70, preferably 5 to 50% by weight, optionally together with a preservative, for example a conventional preservative such as a benzoate, particularly an ester of p-hydroxybenzoic acid such as the methyl, ethyl, n-propyl, n-butyl or benzyl ester thereof or the sodium salt of the ester and other excipients such as dispersing agents and suspending agents.

The present invention also provides a method of preparing a pharmaceutical composition as hereinbefore described which comprises melting a saturated polyalkylene glycol glyceride, mixing a staurosporine active ingredient with the molten glyceride and allowing the resulting mixture to solidify.

The glyceride is conveniently melted by heating to a temperature 10° to 20° C. above its melting point before addition of the staurosporine active ingredient as a powder. Optional excipients may be added to the molten mixture.

When a composition of the invention is to be administered in capsules, for example orally, the liquid mixture of the staurosporine active ingredient and glyceride may be poured into hard capsules or injected into soft capsules and allowed to solidify therein. Alternatively, the solid solution or solid dispersion obtained on cooling the liquid mixture of the staurosporine active ingredient and glyceride may be remelted for introduction into capsules. The capsules may contain, for example, from 1 mg to 250 mg of the staurosporine active ingredient.

When a composition of the invention is to be administered as a dispersion in an aqueous medium, e.g. water, a saline solution or mixture of water with a water-miscible pharmaceutically acceptable solvent, the solid solution or solid dispersion obtained on cooling the liquid mixture is conveniently broken up and dispersed in the aqueous medium by stirring or by ultrasonication.

The compositions of the invention may be used in the treatment of the indications hereinbefore described. The compositions may be administered in prophylactically or curatively effective amounts. For example, compositions containing daily doses of 1 to 1000 mg of the active ingredient may be administered to warm-blooded animals having a body weight of about 70 kg. The compositions are particularly useful in the treatment of cancer.

The invention is illustrated by the following Examples, in which parts are by weight.

EXAMPLE 1

Gelucire 44/14 (82 parts) is melted by heating to 60° C. Powdered N-benzoylstaurosporine (18 parts) is added to the molten material. The resulting mixture is homogenised and the dispersion obtained is introduced into hard gelatin capsules of different size, so that some contain a 25 mg dosage and others a 75 mg dosage of the staurosporine. The resulting capsules are suitable for oral administration.

EXAMPLE 2

Gelucire 44/14 (86 parts) is melted by heating to 60° C. Powdered N-benzoylstaurosporine (14 parts) is added to the molten material. The mixture is homogenised and the dispersion obtained is introduced into hard gelatin capsules of different size, so that some contain a 25 mg dosage and others a 75 mg dosage of the staurosporine. The resulting capsules are suitable for oral administration.

EXAMPLE 3

The bioavailability of N-benzoylstaurosporine dispersed in Gelucire 44/14 is tested as follows:

Dosages of 100 mg of N-benzoylstaurosporine dispersed in 500 mg of Gelucire 44/14 are administered orally in size O gelatine capsules to two healthy random bred pedigree male beagle dogs weighing 10–15 kg.

Blood samples (4 ml) are collected from each dog prior to administration and at various time intervals after administration. Each sample is immediately centrifuged and the separated plasma is protected from light, frozen and stored in the dark at −20° C. until analysed. The concentration of N-benzoylstaurosporine in each plasma sample is determined by high performance liquid chromatography using UV detection. The results are as follows:

| Time (hours) | Concentration of N-benzoylstaurosporine in Plasma ($\mu$ mol/l) | |
| --- | --- | --- |
| | Dog 1 | Dog 2 |
| 0 | 0 | 0 |
| 1 | 0.27 | 0.23 |
| 2 | 0.38 | 0.30 |
| 3 | 0.36 | 0.45 |
| 4 | 0.31 | 0.41 |
| 6 | 0.27 | 0.40 |
| 8 | 0.24 | 0.28 |

What is claimed is:

1. An orally administrable pharmaceutical composition comprising a solution or dispersion of a staurosporine active ingredient in a solid saturated polyalkylene glycol glyceride.

2. A composition according to claim 1, in which the staurosporine active ingredient is a N-acylstaurosporine.

3. A composition according to claim 1, in which the staurosporine active ingredient is N-benzoylstaurosporine.

4. A composition according to claim 3, in which the glycol glyceride is a mixture of esters of one or more $C_8$–$C_{18}$ saturated fatty acids with glycerol and a polyethylene glycol having a molecular weight of 1000 to 2000.

5. A composition according to claim 4, in which the polyethylene glycol has a molecular weight of 1400 to 1600.

6. A composition according to claim 5, in which the staurosporine active ingredient is present in an amount of 10 to 20% by weight of the composition.

7. A composition according to claim 1, in which the glycol glyceride is a mixture of glyceryl and polyethylene glycol esters of one or more $C_8$–$C_{18}$ saturated fatty acids.

8. A composition according to claim 7, in which the glycol glyceride is a mixture of esters of one or more $C_8$–$C_{18}$ saturated fatty acids with glycerol and a polyethylene glycol having a molecular weight of 1000 to 2000.

9. A composition according to claim 8, in which the polyethylene glycol has a molecular weight of 1200 to 1800.

10. A composition according to claim 8, in which the polyethylene glycol has a molecular weight of 1400 to 1600.

11. A composition according to claim 1, in which the staurosporine active ingredient is present in an amount of 1 to 30% by weight of the composition.

12. A composition according to claim 11, in which the staurosporine active ingredient is present in an amount of 5 to 25% by weight of the composition.

13. A composition according to claim 12, in which the staurosporine active ingredient is present in an amount of 10 to 20% by weight of the composition.

14. A composition according to claim 1 contained in a capsule.

15. A composition according to claim 1 as a dispersion in an aqueous medium.

16. A composition according to claim 15, in which the dispersion contains 0.5 to 70% by weight of the composition.

17. A method of preparing a pharmaceutical composition which comprises melting a saturated polyalkylene glycol glyceride, mixing a staurosporine active ingredient with the molten glyceride and allowing the resulting mixture to solidify.

18. A method according to claim 17, in which the glycol glyceride is a mixture of esters of one or more $C_8$–$C_{18}$ saturated fatty acids with glycerol and a polyethylene glycol having a molecular weight of 1000 to 2000.

19. A method according to claim 17, in which the staurosporine active ingredient is N-benzoylstaurosporine.

20. A method according to claim 17, in which the staurosporine active ingredient is used in an amount of 10 to 20% by weight of the composition.

* * * * *